(12) United States Patent
Cosman et al.

(10) Patent No.: US 6,743,226 B2
(45) Date of Patent: Jun. 1, 2004

(54) ADJUSTABLE TRANS-URETHRAL RADIO-FREQUENCY ABLATION

(75) Inventors: Eric R. Cosman, Belmont, MA (US); Francis J. McGovern, Lexington, MA (US)

(73) Assignees: Cosman Company, Inc., Belmont, MA (US); The General Hospital Corporation, Boston, MA (US)

( * ) Notice: Subject to any disclaimer, the term of this patent is extended or adjusted under 35 U.S.C. 154(b) by 292 days.

(21) Appl. No.: 09/780,913

(22) Filed: Feb. 9, 2001

(65) Prior Publication Data

US 2002/0111617 A1 Aug. 15, 2002

(51) Int. Cl.[7] .............................................. A61B 18/18
(52) U.S. Cl. ........................... 606/41; 606/34; 607/99; 607/101
(58) Field of Search ............................. 606/41, 49, 50, 606/34; 607/98, 99, 101, 102, 105, 113, 154

(56) References Cited

U.S. PATENT DOCUMENTS

| | | | |
|---|---|---|---|
| 2,407,690 A | | 9/1946 | Southworth |
| 4,116,198 A | | 9/1978 | Roos |
| 4,184,492 A | | 1/1980 | Meinke et al. |
| 4,411,266 A | | 10/1983 | Cosman |
| 4,565,200 A | * | 1/1986 | Cosman ........................ 606/50 |
| 4,682,596 A | | 7/1987 | Bales et al. |
| 4,785,823 A | | 11/1988 | Eggers et al. |
| 4,966,597 A | | 10/1990 | Cosman |
| 4,967,765 A | | 11/1990 | Turner et al. |
| 4,979,948 A | | 12/1990 | Geddes et al. |
| 5,007,437 A | | 4/1991 | Sterzer |
| 5,061,266 A | | 10/1991 | Hakky |
| 5,112,330 A | | 5/1992 | Nishigaki et al. |
| 5,178,620 A | | 1/1993 | Eggers et al. |

(List continued on next page.)

FOREIGN PATENT DOCUMENTS

| | | |
|---|---|---|
| EP | 0 754 437 A2 | 1/1997 |
| WO | WO 91/13650 | 9/1991 |
| WO | WO 96/00036 | 1/1996 |
| WO | WO 96/00039 | 1/1996 |
| WO | WO 96/34571 | 11/1996 |
| WO | WO 96/37158 | 11/1996 |
| WO | WO 97/28840 | 8/1997 |
| WO | WO 97/00646 | 9/1997 |
| WO | WO 97/00647 | 9/1997 |
| WO | WO 98/27881 | 12/1997 |

OTHER PUBLICATIONS

US 5,326,343, 7/1994, Rudie et al. (withdrawn)

Bhanot, et al. "A Radiofrequency Method of Thermal Tissue Ablation for Benign Prostatic Hyperplasia," *Urology*, Mar. 1995, vol. 45: pp 427–433.

(List continued on next page.)

*Primary Examiner*—Henry Bennett
*Assistant Examiner*—Fadi H. Dahbour
(74) *Attorney, Agent, or Firm*—Steptoe & Johnson LLP

(57) ABSTRACT

A device for enlarging a urethral passage includes an elongate member having a distal portion configured for intraurethral placement in the urethral passage, and an electrode at the distal portion. The electrode is configured to be energized with high frequency energy to necrose tissue of the urethral wall and surrounding prostate tissue to form a cavity in the urethral passage. The electrode has an adjustable working length. The electrode has a diameter greater than about 16 French to substantially occlude the urethra. The device includes multiple electrodes spaced apart a distance of about 1 to 5 mm to provide flexibility in the distal portion of the elongate member. A method of treating a urethral passage includes measuring a length of a patient's prostate, and selecting a length of an electrode based on the measured length of the prostate.

20 Claims, 7 Drawing Sheets

U.S. PATENT DOCUMENTS

| | | | |
|---|---|---|---|
| 5,220,927 A | 6/1993 | Astrahan et al. | |
| 5,249,585 A | 10/1993 | Turner et al. | |
| 5,257,977 A | 11/1993 | Eshel | |
| 5,263,931 A | 11/1993 | Miller | |
| 5,277,201 A | 1/1994 | Stern | |
| 5,300,099 A | 4/1994 | Rudie | |
| 5,301,687 A | 4/1994 | Wong et al. | |
| 5,304,214 A | 4/1994 | DeFord et al. | |
| 5,322,507 A | 6/1994 | Costello et al. | |
| 5,330,518 A | 7/1994 | Neilson et al. | |
| 5,348,554 A | 9/1994 | Imran et al. | |
| 5,370,675 A | 12/1994 | Edwards et al. | |
| 5,370,677 A | 12/1994 | Rudie et al. | |
| 5,403,311 A | 4/1995 | Abele et al. | |
| 5,413,588 A | 5/1995 | Rudie et al. | |
| 5,454,809 A | 10/1995 | Janssen | |
| 5,464,437 A | 11/1995 | Reid et al. | |
| 5,464,445 A | 11/1995 | Rudie et al. | |
| 5,472,441 A | 12/1995 | Edwards et al. | |
| 5,480,417 A | 1/1996 | Hascoet et al. | |
| 5,486,161 A | 1/1996 | Lax et al. | |
| 5,492,529 A | 2/1996 | Neuwirth et al. | |
| 5,509,929 A | 4/1996 | Hascoet et al. | |
| 5,520,684 A | 5/1996 | Imran | |
| 5,542,915 A | 8/1996 | Edwards et al. | |
| 5,545,137 A | 8/1996 | Rudie et al. | |
| 5,545,161 A | 8/1996 | Imran | |
| 5,575,811 A | 11/1996 | Reid et al. | |
| 5,599,294 A | 2/1997 | Edwards et al. | |
| 5,599,346 A | 2/1997 | Edwards et al. | |
| 5,620,480 A | 4/1997 | Rudie | |
| 5,628,770 A | 5/1997 | Thome et al. | |
| 5,630,426 A | 5/1997 | Eggers et al. | |
| 5,643,335 A | 7/1997 | Reid et al. | |
| 5,645,528 A | 7/1997 | Thome | |
| 5,681,282 A | 10/1997 | Eggers et al. | |
| 5,697,909 A | 12/1997 | Eggers et al. | |
| 5,733,316 A | 3/1998 | Tierney et al. | |
| 5,755,754 A | 5/1998 | Rudie et al. | |
| 5,810,764 A | 9/1998 | Eggers et al. | |
| 5,849,011 A | 12/1998 | Jones et al. | |
| 5,891,134 A | 4/1999 | Goble et al. | |
| 5,944,715 A | 8/1999 | Goble et al. | |
| 6,171,306 B1 | 1/2001 | Swanson et al. | |
| 6,440,127 B2 * | 8/2002 | McGovern et al. | 606/41 |
| 6,447,505 B2 * | 9/2002 | McGovern et al. | 606/41 |
| 6,506,189 B1 * | 1/2003 | Rittman, III et al. | 606/41 |
| 6,517,534 B1 * | 2/2003 | McGovern et al. | 606/41 |
| 6,530,922 B2 * | 3/2003 | Cosman et al. | 606/34 |

OTHER PUBLICATIONS

Blute, Michael L., et al., "Transurethral Microwave Thermotherapy for Management of Benign Prostatic Hyperplasia: Results of the United States Prostatron Cooperative Study," *Journal of Urology*; Nov., 1993; vol. 150, No. 5, Part 2 of 2; pp 1591–1596.

Brochure, SMK Sluijter–Mehta Kits, "The Finest Radiofrequency Electrodes for Pain Therapy" Radionics, Burlington, MA, 1996.

Cosman et al., "Theoretical Aspects of Radiofrequency Lesions in the Dorsal Root Entry Zone" *Neurosurgery*, vol. 15, No. 6, pp 945–950, Dec. 1984.

Costello et al., "Nd:YAG Laser Ablation of the Prostate as a Treatment for Benign Prostatic Hypertrophy", *Lasers in Surgery and Medicine*, vol. 12, No. 2; pp 121–124, 1992.

Dawkins, et al. "Radiofrequency heat–treatment to the prostate for bladder outlet obstruction associated with benign prostatic hyperplasia: a 4–year outcome study," *British Journal of Urology*, vol. 79, pp. 910–914 (1997).

Djavan, et al. "Minimally Invasive Procedures and Medical Management—Their Relative Merits in Treating Lower Urinary Tract Symptoms of Benign Prostatic Hyperplasia", *Reviews in Urology*, vol. 2; pp 105–114 (2000).

Goldberg et al., "Tissue Ablation with Radiofrequency: Effect of Probe Size, Gauge, Duration, and Temperature on Lesion Volume" *Acad. Radiol.*, vol. 2, No. 5, pp 399–404, May 1995.

Goldwasser, B., et al., "Transurethral Needle Ablation (TUNA) of the Prostate Using Low–Level Radiofrequency Energy: An Animal Experimental Study," *European Urology*; Oct., 1993; vol. 24; pp 400–405.

Harada et al., "Microwave Surgical Treatment of Diseases of Prostate" *Urology*, vol. XXVI, No. 6, pp 572–576, Dec. 1985.

Kramolowsky, et al. "The Urological Application of Electrosurgery," *The Journal of Urology*, vol. 146, pp 669–674, Sep. 1991.

Kramolowsky, et al, "Use of 5f Bipolar Electrosurgical Probe in Endoscopic Urological Procedures," *The Journal of Urology*, vol. 143, pp 275–277, Feb. 1990.

McGahan et al., "Percutaneous Ultrasound–Guide Radiofrequency Electrocautery Ablation of Prostate Tissue in Dogs" *Acad Radiol.*, 2:61–65, 1995.

Nardella, "Radio Frequency Energy and Impedance Feedback," *SPIE*, vol. 1068, pp 42–48 (1989).

Onik et al., "Transrectal Ultrasound–Guided Percutaneous Radical Cryosurgical Ablation of the Prostate," *Cancer*; Aug. 15, 1993; vol. 72, No. 4; pp 1291–1299.

*Radionics Neurosurgical Instruments*, Trigeminal Neralgia Kit Description (1981).

Schulman, Claude C., et al., "Transurethral Needle Ablation (TUNA): Safety, Feasibility, and Tolerance of a New Office Procedure for Treatment of Benign Prostatic Hyperplasia," *European Urology*; vol. 24; pp 415–423; 1993.

Solbiati, et al., "Hepatic Metastases: Percutaneous Radio–Frequency Ablation with Cooled–Tip Electrodes," *Radiology*; Nov., 1997; vol. 205, No. 2; pp 367–373.

Sunshine, Robert D., M.D., et al., "Complications of Transurethral Resection of the Prostate," *Urologic Complications, Medical and Surgical, Adult and Pediatric*, 1986; Chapter 18; pp 231–246.

Thermex Clinical Data, Direx Medical Systems, Nov. 1993.

Tuckers, et al, "A Comparison of Urologic Application of Bipolar Versus Monopolar Five French Electrosurgical Probes," *The Journal of Urology*, vol. 141, pp 662–665, Mar., 1989.

Turapy Clinical Data, Direx Medical Systems, undated.

* cited by examiner

ADJUSTABLE TRANS-URETHRAL RADIO-FREQUENCY ABLATION

FIELD OF THE INVENTION

This invention relates generally to advances in medical systems and procedures for prolonging and improving human life. More particularly, this invention relates to an improved method and system for alleviating urinary obstruction caused by enlargement of the prostate by performing thermal high frequency ablation for urethral enlargement.

BACKGROUND OF THE INVENTION

A majority of all males over 60 years old experience partial or complete urinary obstruction because of the enlargement of the prostate. This condition usually originates from benign prostatic hyperplasia (BPH), which is an increase in cell mass near the urethra, or less likely, from prostate cancer. Both of these conditions involve an increase in prostatic tissue mass, which in its increased state encroaches on the urethra and obstructs the urinary pathway.

In the case where urinary obstruction is caused by BPH, a common treatment involves a medical procedure using a side-cutting instrument and/or endoscope to surgically enlarge a passageway for urine flow through the prostate. The side-cutting instrument, which is typically passed through an endoscopic tube, is passed through the penis into the urethra and is used to surgically remove prostate tissue and part of the urethra at the point of the obstruction. This procedure is referred to as "Trans-urethral Resection of the Prostate" (or "TURP"). Typically, the TURP procedure removes more than superficial tissue layers, that is, more than a diameter of 10 millimeters around the urethra, since the BPH condition could advance, creating repeated BPH obstruction. Using the TURP procedure, the surgical cavity that is created in the prostate can be tailored to the prostate size, both in length and diameter. The TURP procedure can also avoid critical structures such as the bladder neck, the rectal wall, which is adjacent to the prostate, and the erectile nerves at the border the prostate on the rectal side.

In the case where urinary obstruction results from prostate cancer, surgical prostatectomies are commonly used to eliminate the obstruction.

In recent years, less invasive systems and procedure that inflict less trauma on the patients have been attempted. One such procedure, called "Trans-urethral Needle Ablation" (or "TUNA"), involves passing a radio-frequency (RF) instrument such as a catheter, cannula, sheath, or scope into the urethra. The RF instrument houses special RF electrode tips that emerge from the side of the instrument. The tips are pushed out of the instrument along off-axis paths to pierce the urethral wall and pass into the prostatic tissue outside of the urethra. The TUNA system and procedure attempts to leave the urethra intact and uninjured by the application of RF heating.

Another minimally invasive technique for treating BPH is Trans-urethral Microwave Thermo Therapy (or "TUMT"). This involves use of a cooled catheter which also delivers heat energy to the prostate. A catheter that has a microwave probe inside of it is inserted into the urethra to the point of the prostate. The microwave probe is typically a microwave antenna which is located inside the catheter near its distal end and is connected to an external generator of microwave power outside the patient's body. In this way the prostate is heated by radiative electromagnetic heating. At the same time the catheter is cooled by circulation of a coolant fluid within the catheter. The objective is to cool the urethra and thereby to prevent damage to it by the heating process which is occurring in the prostatic tissue that is outside of and at a distance from the urethra. Thus, the TUMT procedure seeks to preserve the urethra and the prostatic tissue immediately outside of the urethra by cooling the catheter with fluid coolant that is circulated within the catheter. In the TUMT procedure, the prostatic tissue immediately around the urethra and the urethra itself are deliberately spared from receiving an ablative level of heating, that is, the temperatures for these structures are less than 50 degrees C.

It should be recognized that the theory behind and practice of RF heat ablations has been known for decades, and a wide range of RF generators and electrodes for accomplishing such practice exist. For example, equipment for performing heat lesions is available from Radionics, Inc., located in Burlington, Massachusetts. Radio-frequency (RF) ablation is well known and described in medical and clinical literature. To that end, a research paper by E. R. Cosman, et al., entitled "Theoretical Aspects of Radio-frequency Lesions in the Dorsal Root Entry Zone," *Neurosurgery*, vol. 15, no. 6, pp. 945–950 (1984), describing various techniques associated with radio-frequency lesions, is hereby incorporated by reference herein in its entirety. Also, a research paper by S. M. Goldberg, et al., entitled "Tissue Ablation with Radio-frequency: Effect of Probe Size, Gauge, Duration, and Temperature on Lesion Volume," *Acad. Radiol.*, vol. 2, pp. 399–404 (1995), describes techniques and considerations relating to tissue ablation with radio-frequency energy, and is hereby incorporated by reference herein in its entirety.

SUMMARY OF THE INVENTION

According to the invention, a device for enlarging a urethral passage includes an elongate member having a distal portion configured for intraurethral placement in the urethral passage, and an electrode at the distal portion of the elongate member. The electrode is configured to be energized with high frequency energy to necrose tissue of the urethral wall and surrounding prostate tissue to form a cavity in the urethral passage. The electrode has an adjustable working length.

Embodiments of this aspect of the invention may have one or more of the following features.

A removable insulative member covers at least a portion of the electrode. The device includes an insulating sleeve and the electrode is movable relative to the insulating sleeve to adjust the working length. The electrode has a diameter greater than about 16 French to substantially occlude the urethra. The electrode is disposed on an outer surface of the distal portion of the elongate member. The device includes multiple electrodes at the distal portion of the elongate member, and multiple wires each for independently coupling one of the multiple electrodes to a high frequency electrical signal. The electrodes are spaced apart a distance of about 1 to 5 mm.

According to another aspect of the invention, a device for enlarging a urethral passage includes an elongate member having a distal portion configured for intraurethral placement in the urethral passage, and a plurality of electrodes at the distal portion of the elongate member. The electrodes are configured to be energized with high frequency energy to necrose tissue of the urethral wall and surrounding prostate tissue to form a cavity in the urethral passage. The electrodes are spaced apart a distance of about 1 to 5 mm to provide flexibility in the distal portion of the elongate member.

Embodiments of this aspect of the invention may include one or more of the following features.

The electrodes have a diameter greater than about 16 French to substantially occlude the urethra. The device includes multiple wires each for independently coupling one of the multiple electrodes to a high frequency electrical signal. The high frequency electrical signal can be selectively applied to each of the electrodes to adjust a length of the region of ablative heating. The electrodes are disposed on an outer surface of the distal portion of the elongate member. A removable insulative member covers at least a portion of one of the electrodes.

According to another aspect of the invention, a method of treating a urethral passage includes measuring a length of a patient's prostate, and selecting a length of an electrode based on the measured length of the prostate. The electrode is configured to be energized with high frequency energy to necrose tissue of the urethral wall and surrounding prostate tissue to form a cavity in the urethral passage.

Embodiments of this aspect of the invention may include one or more of the following features.

The electrode includes multiple electrodes and the step of selecting includes determining which electrode to energize. The step of selecting includes removing insulation from the electrode. The step of selecting includes advancing an electrode relative to an insulating sleeve.

The method includes selecting a diameter of the electrode that substantially occludes the urethra, and energizing the electrode with high frequency energy to elevate the temperature of the urethra to at least 50° C. to ablate tissue of a wall defining the urethral passage and ablate adjacent prostate tissue to form a cavity communicating with the urethral passage.

Advantages of the invention may include a minimally invasive ablation technique that simulates the advantages of TURP, for example, tailoring the formed cavity or void according to the length of the prostate and producing a cavity diameter that is beyond the superficial tissue layers around the urethra, that is cavity diameters greater than about 10 to 12 millimeters. An ablation volume within and around the prostatic urethra is created minimally invasively in accordance with the size of the patient's prostate and other clinical criteria such as the preservation or non-preservation of the bladder neck, and matching the physiologic anatomy and size of the urethra and prostate for a specific patient.

The technique requires a very short time to perform, for example, less than ten minutes and preferably in the range of two to six minutes, in which time the patient can be maintained comfortably without undue anesthetic and without experiencing undue pain or distress. The procedure can be performed in a doctor's office or in an outpatient setting, without requiring an operating room or extensive, sophisticated personnel such as anesthesiologists and nurses.

The ablation is performed for the treatment of BPH and the associated alleviation of urethral obstruction. The ablation can also be used to treat other diseases such as prostate cancer to alleviate urethral obstruction.

The details of one or more embodiments of the invention are set forth in the accompanying drawings and the description below. Other features, objects, and advantages of the invention will be apparent form the description and drawings, and from the claims.

BRIEF DESCRIPTION OF THE DRAWINGS

In the drawings which constitute a part of the specification, embodiments exhibiting various forms and features hereof are set forth, specifically.

DETAILED DESCRIPTION OF THE INVENTION

Figure 1:
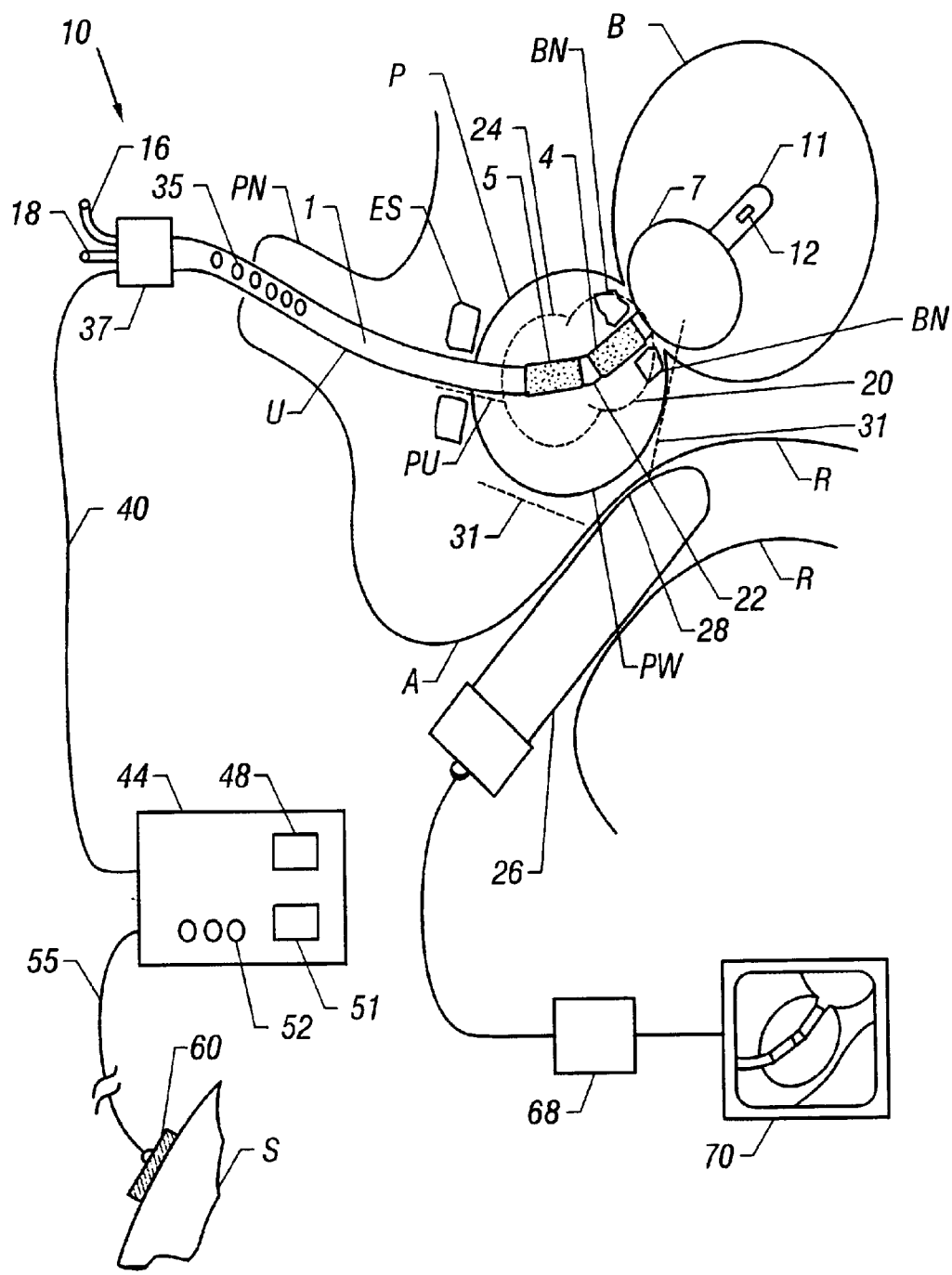
FIG. 1 is a schematic diagram showing a portion of a patient along with a system according to the invention for performing intraurethral thermal ablation of the urethra and central prostate.

Referring to FIG. 1, in a system 10 in accordance with the present invention, an elongated probe 1 is inserted via the penis PN into the urethra U of a living body such as a patient, and into an operative field within the patient's body, specifically including the prostate gland P. In this exemplary embodiment, probe 1 is a flexible rubber catheter that facilitates introduction of the probe into the urethra. Probe 1 has a distal, rounded tip 11 and a drainage hole 12. When located inside the patient's bladder B, drainage hole 12 allows irrigation and flushing of the contents of the bladder via fluid channels 16 within probe 1. Probe 1 has a balloon 7 inflated via an inflation channel 18 within probe 1. Once placed within bladder B, balloon 7 is used to anchor the position of probe 1 by applying a pulling or tension force on probe 1 so that balloon 7 is brought tightly against the bladder neck BN portion of the prostate.

Probe 1 has conductive electrode elements 4 and 5, which are positioned on the rubber substrate of probe 1 such that when balloon 7 is brought snugly against the bladder neck BN, electrodes 4 and 5 are appropriately positioned within the prostate to perform thermal prostatic ablation. The course of the prostatic urethra PU and external urethra U has significant and acute curves from the penis into the bladder, and flexibility of the probe structure 1 and the portion of the probe near electrodes 4 and 5 is advantageous to facilitate insertion of the catheter and for patient comfort. Between electrodes 4 and 5 is a gap 22 formed by the insulative rubber substrate of probe 1. When the length of gap 22 is appropriately chosen, for example, in the range of 1 to 6 mm or more, there is sufficient flexibility between electrodes 4 and 5 to easily introduce probe 1 into the external urethra U and the prostatic urethra PU without patient discomfort. Spaced electrodes 4 and 5 allow heat ablation to be done in a sequential, segmented fashion with each electrode activated separately to produce zones of ablation, as illustrated by dashed line 20, associated with the heat ablation zone for electrode 4, and dashed line 24, associated with the heat ablation zone for electrode 5. With a sufficiently small gap 22, for example, 1 to 5 millimeters, zones 20 and 24 overlap so the aggregate ablation zones does not have discontinuities or undesired irregularities in shape.

System 10 includes an ultrasonic imaging device 26, which is placed intra-rectally through the anal opening A. Device 26 has an imaging head 28, for example, an ultrasonic scanning transducer, which rests against the rectal wall R near the prostate T. The ultrasonic imaging device 26 may be any common tool used in diagnostic medicine, for example, Accuson, Inc., located in Mountain View, Calif., provides several suitable ultrasonic imaging devices. Imaging head 28 scans the region of tissue falling within, for example, the area bounded by the dashed lines 31, to generate a visual image. This image may include the rectal wall R, the prostate, the urethra, and the electrode elements 4 and 5. The ultrasonic scanning head 28 is connected to an ultrasonic image processing unit 68 and a display unit 70, as is common practice. The display 70 provides real-time ultrasonic images of the prostate with the position of electrodes 4 and 5 shown relative to the prostate P, the bladder neck BN, and the bladder B to confirm the position of the electrodes and the probe within the prostate prior to heat ablation.

Positioning of electrodes 4 and 5 within the prostate is important, since it determines where the ablation volumes 20 and 24 will occur and whether the ablation volumes will impinge on critical structures. One critical structure is the external sphincter ES. This is located at the so-called "apex end" of the prostate P, just outside the prostate and surrounding the urethra U in that region. The external sphincter controls urinary function, and if damaged by heat ablation can leave the patient incontinent. Thus it is very important in the treatment of BPH to spare the external sphincter. Thus it is important that ablation zone 24 does not spread into the external sphincter, causing permanent damage. Another critical structure is the bladder neck BN located at the bladder end of the prostate B, and containing the internal sphincter, which surrounds the prostatic urethra in that region. The bladder neck controls aspects of sexual function, including providing means to prevent retrograde ejaculation. Surgeons performing the TURP procedure sometimes will spare the bladder neck BN, and sometimes will not spare the bladder neck, depending on clinical indications. In the case of the present invention, one objective is for the urologist to have the option to spare or not spare the bladder neck for the same considerations that would be given for a TURP surgical procedure. Another critical region is the posterior prostatic wall PW. It is closest to the rectal wall R and also close to critical nerves associated with sexual performance that run between the posterior wall PW and the rectal wall R. These nerves, in part, control erectile function and if they are damaged can lead to impairment. The spread of heat ablation zones 20 and 24 could cause damage to these critical areas. These clinical considerations are used to determine the selected length and position of the electrodes and the time and temperature parameters of the heat ablation process.

Electrodes 4 and 5 are connected to an external generator 44 by internal wires (not shown) within probe 1. The wires provide separate connections for the electrodes 4 and 5 into a hub 37 pf probe 1. Hub 37 is connected to generator 44 by an external connection 40. The generator 44 is a source of high frequency electrical voltage or current that can be applied through the connection 40 and the internal wires within probe 1 to electrodes 4 and/or 5 to produce heat ablation in the prostate. For example, RF voltage applied from the generator to electrode 4 causes RF current to emanate through the urethral and peri-urethral tissue of the prostate located near to and in the region of electrode 4. The RF current has its highest concentration near the electrode 4 and falls off as the distance from electrode 4 increases. In a typical arrangement, the current returns to the generator through a large-area reference electrode 60 placed elsewhere on the skin S of the patient's body and connected to the generator 44 by a cable 55. The RF current within the tissue produces energy deposition in the tissue at a distance from the electrode due to the electrical resistivity of the tissue. It is the electromechanical dissipation of this deposited RF energy in the tissue that causes the tissue to heat up near the electrode 4. Tissue heating to greater than approximately 50° C. for several minutes causes death of the cells and constituents of the tissue. The temperature falls off from the region near the electrode 4 and defines a zone of 50° C. temperature, which is the isotherm associated with the ablation volume, as illustrated by the dashed curve 20 in FIG. 1.

The dimensions and size of the ablation volume 20 may be increased by increasing the output power from the generator 44 through the electrode 4 and is influenced by the geometry of the electrode 4. Thus, the size and volume of the ablation zone 20 can be graded and controlled around the urethral channel near the electrode by choice of RF generator parameters, electrode geometry, and the time of treatment. For example, an electrode 4 having a length of 15 mm and a diameter of 7 to 8 mm used to heat the adjacent tissue to 70° C. for three minutes creates an ablation volume with a diameter of about 20 mm and a length of about 21 mm. Increasing the treatment time to five minutes increases the ablation diameter to about 24 mm. When electrode 4 is used to heat the adjacent tissue to 80° C. for three minutes, the ablation diameter is about 28 mm. Increasing the treatment time to five minutes increases the ablation diameter to about 30 mm.

The generator 44 can have many control and readout functions associated with the RF parameters of the ablation process. These are illustrated in FIG. 1 by meters 48 and 51, which display output power, current, voltage, impedance, or other parameters associated with the heating process. Also, control aspects of the generator illustrated by element 52 can manually, automatically, or by computer control govern and monitor the process and parameter display of RF signal application to the electrodes and time parameters during the procedure. The generator 44 is, for example, a high frequency generator with various possible frequency ranges: several tens of kilohertz to 100 kilohertz; 100 kilohertz to 1 megahertz; 1 megahertz to several megahertz or several hundred megahertz, or even greater frequencies are possible. Radiofrequencies in the 100 kilohertz to 100 megahertz are effective. Connection cable 40 can, for example, deliver RF output to electrode 4 individually, electrode 5 individually, electrodes 4 and 5 in combination, or electrodes 4 and 5 in a bipolar electrical arrangement. In a bipolar configuration, current flows between the electrodes 4 and 5, and the tissue surrounding the electrodes acts as a bodily ionic medium through which the current has a volumetric current pathway between the electrodes.

Probe 1 includes index markers 35 that provide a gauge of the depth of the probe within the urethra with the markers referenced to the external urethra by the penis PN. Markers 35 help in positioning the catheter and electrodes within the prostate and/or act as a check that the electrodes do not move during RF treatment.

Generator 44 has a power range from, for example, 0 to 50 watts or more. Probe 1 can include temperature sensors (not shown) such as thermocouple sensors built into the electrodes 4 and/or 5. The temperature sensor is connected via connector wires extending inside the shaft of probe 1 to the energy source 44 through the connection cable 40. The measured temperature at the electrode is representative of the temperature of the urethra and very nearby prostatic tissue as the RF heat ablation proceeds. The temperature can be displayed on the meter 48 so that the clinician can monitor the progress of the ablation.

The probe 1 has a length of, for example, approximately 20 to 30 centimeters. The diameter of electrodes 4 and 5 is, for example, greater than 16 French (5.3 millimeters) and preferably in the range of 18 to 27 French (6 to 9 millimeters) to effectively occlude the prostatic urethra and provide complete contact of the electrode to the urethral tissue. A 20 French probe 1 accommodates nearly all urethras comfortably.

Figure 2:
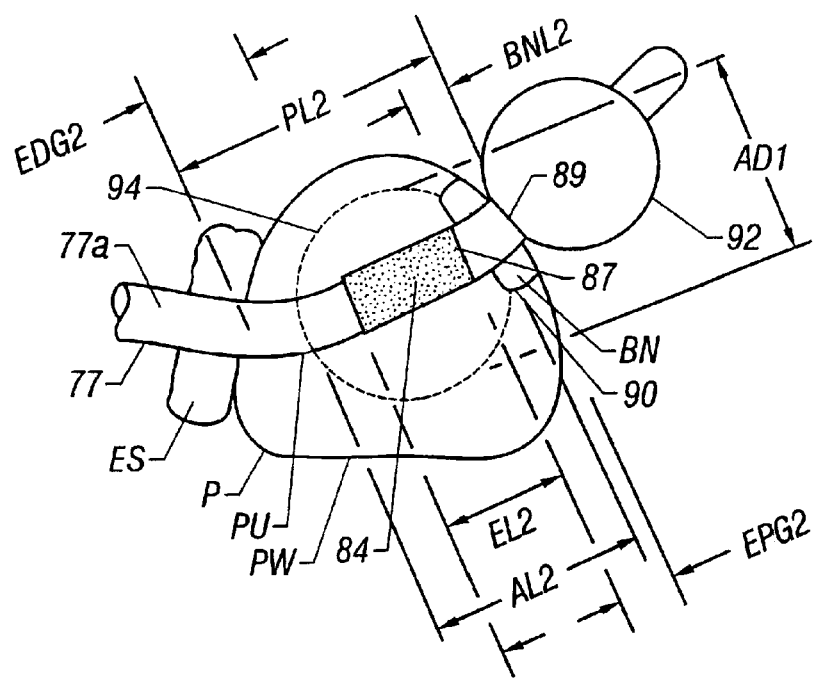
FIG. 2 shows an embodiment of a prostate ablation catheter passed into the urethra in accordance with the present invention.

Referring to FIG. 2, the external sphincter ES surrounds the urethra and is adjacent to the external side or apex end of the prostate as the prostatic urethra PU exits the prostate P. The bladder neck BN representing the portion of the prostate next to the bladder includes the internal sphincter. The margin of the internal sphincter is indicated by the line 90. The length of the prostate is shown as PL2 and is typically defined as the length of the prostatic urethra PU from the exit margin of the prostatic urethra from the prostate at the external sphincter end to the exit margin 89 of the prostatic urethra at the bladder end. Another definition of the prostatic length PL2 is from the bladder neck margin 89 to the verumontanum, which is an anatomical landmark in the prostatic urethra very close to the position of the exit of the prostatic urethra at the external sphincter end of the prostate P. The thickness of the internal sphincter or bladder neck BN is shown as BNL2.

As shown in FIG. 2, a probe 77 is formed by a flexible catheter 77a made from, for example, plastic or similar material such as silicone, latex, polyurethane, polyethylene. Probe 77 includes a conductive RF electrode 84 disposed on the surface of probe 77, and a balloon 92 for fixing or anchor the RF electrode's position within the prostate. The active electrode length is shown as EL2, and is the length of the conductive electrode surface 84. A region of heat ablation produced by penetrating radio-frequency energy deposition into the prostate tissue around the electrode 84 causes cell death and necrosis within an ablation volume indicated by the dashed line 94. The dashed line 94 corresponds approximately to a 50° C. isotherm volume boundary. All tissue within that 50° C. isotherm margin, or ablation volume margin 94, is killed. The length of the ablation volume is shown in FIG. 2 as AL2, and the diameter of the lesion volume is designated AD1. There is a variation in temperature within the ablation volume so that if the boundary 94 corresponds to a 50° C. isotherm, tissue within the volume and closer to the electrode 84 is at a higher temperature.

Subsequent to an RF ablation, with an applied duration or RF heating of a minute or several minutes, the cells within the isotherm 94 die, and within several days or a few weeks the dead cells liquefy and no longer have the usual integrity of living cells. This region of obliteration will, in the course of several days after treatment, form a cavity with a margin corresponding to the dashed line 94. The cavity is contiguous with the prostatic urethra on each end outside the ablation volume, and thus serves to remove prostatic mass and unobstruct the prostatic urethral region that is affected by the BPH disease. Removal of the probe 77 after several days or approximately two weeks following the RF ablation results in the debris from the necrotic cells in the ablated zone being flushed out of the cavity within margin 94 via the urine, leaving a cavity or void in the prostate. Thus, a portion of the prostatic urethra and a portion of the tissue that surrounds the urethra are obliterated by the RF heat ablation process.

The configuration and positioning of the RF electrode within the prostate is selected to tailor and match the associated ablation volume to the size and geometry of the prostate and/or to specific clinical considerations of the extent of the ablation volume desired. In FIG. 2, the ablation volume, represented by the line 94, approximates the length of the prostate PL2 and achieves a significant ablation diameter AD1. The size, position, length, and diameter of the ablation volume 94 approximate the size of a cavity in the prostate achieved by the surgical TURP procedure, discussed above. Thus the ablation diameter AD1 surpasses the intermediate zone around the urethra (approximately 10 millimeters diameter) achieving a diameter of 20 millimeters or more. This requires penetration of the ablation volume well beyond the prostatic urethra and superficial periurethral tissue (tissue within a radial distance of about 5 millimeters from the surface of the electrode 84). RF current emanating from electrode 84 heats the tissue at a distance from the electrode. The current spreads from the electrode 84 into the tissue and causes frictional heating within the tissue mass by the oscillatory motion of the ionic tissue medium. The heat deposition in the surrounding tissue of the prostate is deposited immediately without relying on thermal convection to spread into the tissue volume near the electrode. Thus the heating process can take place rapidly, which increases the efficiency of the procedure, the safety, and the comfort to the patient.

The electrode length EL2 is selected to form an ablation length AL2 that approximates a measured prostate length PL2. By natural human physiology, there is a wide range of prostate lengths PL2, for example, from about 25 millimeters to 60 millimeters or more. When it is desired to spare the bladder neck or leave a few millimeters of unablated margin at the apex end of the prostatic urethra, the electrode length EL2 is chosen to be somewhat shorter than PL2. The position of electrode 84 in relation to the adjacent margin 89 of the balloon 92 determines whether the RF ablation margin 94 engulfs the bladder neck BN. The gap between the electrode and the proximal margin of the balloon 89 is designated as EPG2. This is a selectable dimension that determines if the RF ablation includes the bladder neck. If the gap EPG2 is sufficiently small, for example, within the range of 0 to 3 millimeters, the ablation margin 94 spreads in the direction of the bladder encroaching on or engulfing the region of the bladder neck BN (within margin 90), as indicated in FIG. 2. With a larger gap EPG2, for example, 5 to 7 millimeters, or 7 to 10 millimeters, the dashed line 94 does not overlap the bladder neck BN, and thus the bladder neck BN is spared. If desired, the electrode length can be selected to leave a margin at the end of the prostatic urethra nearest the external sphincter so that there is no danger of ablation of the external sphincter. Thus, the length of the electrode 84 is preferably selectable or adjustable by the urologist. In use, the urologist first measures the prostatic length PL2 of the patient. Based upon a consideration of what anatomical features to preserve, the length of the electrode 84 and the length of the gap between the electrode and bladder EPG2 are selected.

Catheter 77a has a diameter of, for example, 20 French (6.7 millimeters) (which is typical for some urological catheters), 18 French, 16 French, or smaller. The electrode 84 is, for example, a metallic cylindrical ring that is affixed over or to the external surface of the catheter 77a. Electrode 84 has a diameter of, for example, greater than 16 French (5.3 millimeters) such as: 6 mm; or 7 mm; or 8 mm; or 9 mm; or 10 mm, depending on the diameter of the patient's urethral. Electrode 84 has a length of, for example, 15 millimeters. The probe diameter can be significantly smaller, for example, 2 to 5 French smaller, than the electrode diameter to provide increased flexibility while maintaining an occlusive diameter for the electrode. The wall thickness of electrode 84 is in the range of, for example, 0.001 millimeters to 1 millimeter or more. Any spacing between the electrode and the catheter can be filled in with, for example, silicone. A temperature sensor can be located between catheter 77a and electrode 84 or imbedded in electrode 84.

Connecting a 15 mm long ring electrode 84 to an RF generator, raising the RF power to a level so that the urethral temperature adjacent to electrode 84 is 70° C., and maintaining that temperature for three minutes, produces an ablation volume with a length AL2 of approximately 19 to 21 millimeters and an ablation diameter AD1 of approximately 20 millimeters. Selecting the proximal electrode gap EPG2 beforehand to be approximately 3 millimeters or less results in the ablation volume 94 encompassing most or all of the bladder neck BN, including the internal sphincter. However, selecting a gap EPG2 of approximately 5 millimeters or more results in the ablation volume not eclipsing a substantial portion of the internal sphincter, thus sparing the bladder neck.

The ablation volume length AL2 is such that the ablation margin 94 extends approximately 2 to 3 millimeters beyond the ends of the electrode 84. Thus, at the distal end of the electrode 84 closest to the external sphincter, a sufficient electrode distal gap, designated as EDG2, can be selected to avoid damage to the external sphincter. Thus, for example, if the gap EDG2 is greater than approximately 5 millimeters, the ablation border 94 is 2 millimeters or more from the margin of the external sphincter. Thus, a 15 mm long electrode is suitable for a prostate having a length PL2 of 20 to 25 millimeters. Longer electrodes accommodate longer prostates, for example, an electrode length of 20 millimeters is suitable for prostate lengths of 25 to 30 millimeters, and electrode lengths EL2 of 25, 30, 35, 40, 45, 50 and 60 millimeters can be selected to accommodate longer prostates.

The electrode 84 is, for example, an annular ring, metal braid, surface fiber, coating, wire helix, coil, or wire segment, made from, for example, stainless steel, titanium, nickel alloys, platinum alloys, or copper with surface plating. The probe 77 can be supplied to the urologist in different models with different length electrodes 84, which the clinician can select for a specific patient.

Figure 3:
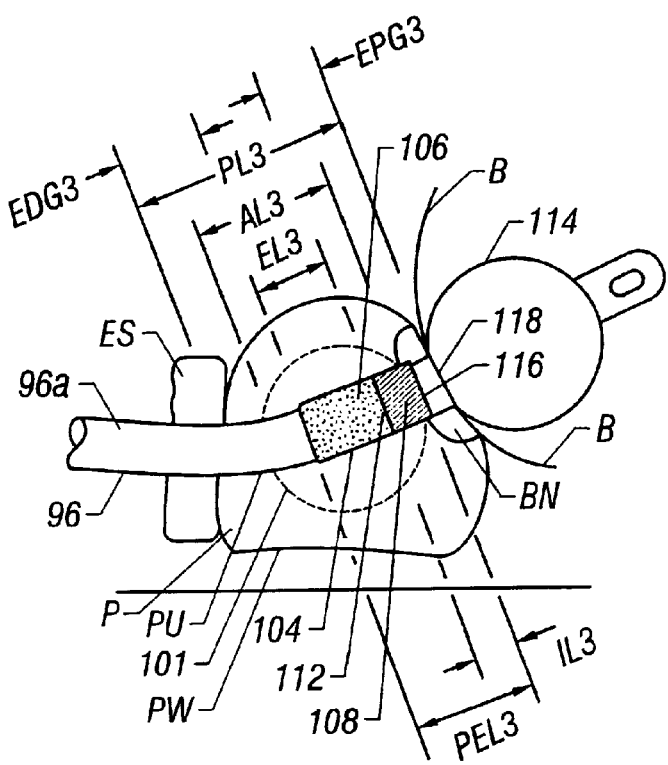
FIG. 3 shows another embodiment of the prostate ablation electrode having an insulative band according to the present invention.

Referring to FIG. 3, a probe 96 includes a catheter 96a and an adjustable length RF electrode 104. RF electrode 104 is disposed on the surface of the catheter 96a, and has an exposed, electrically conductive surface portion 106 having length EL3, and a non-electrically exposed portion 108 covered by an insulating sheath. The length of the insulated, non-exposed portion 108 of the electrode is designated as IL3. An RF ablation volume with margin indicated by the dashed line 101 has an ablation length AL3. The length of the insulated portion 108 of the electrode 108 is selected or adjusted to assure that the heat ablation margin 101 does not extend into the bladder neck BN. To this end, the proximal margin 112 of the electrically exposed electrode portion 104 should be at a sufficient gap distance, specified as EPG3, from the bladder neck margin 118. If it is decided based on clinical conditions to destroy the bladder neck BN by heat ablation, the urologist can remove the insulation covering the electrode 104 in the region 108 to enlarge the length of the exposed RF electrode in the direction of the bladder interface 118. The exposed length of the RF electrode can be adjusted from EL3 to a potential length of PEL3, depending on the degree of removal of the insulation portion 108.

The insulative covering is, for example, an insulative tape, a heat shrunk insulative tubing, or a removable insulative coating that the urologist can remove in part or in whole. Margin 112 can be adjustable by the urologist by using a blade to cut along the circumference of the insulative band, removing selected portions and thus adjusting or varying the margin 112 as desired. One or more selectable, discrete insulative bands can be placed on the electrode, or the urologist can remove sections of insulation coverings to verniate the length of the RF electrode to any desired amount. This will in effect verniate the length of ablative cavity produced by RF heating. The proximal margin 116 of the overall potential RF electrode structure 104 is, for example, within 1, 2, or 5 millimeters of margin 118. The length IL3 of the insulated band portion 108 is, for example, 1 millimeter to 5 millimeters, or more. If the margin 116 is within 2 millimeters of the bladder neck margin 118, and the insulative sheath has length IL3 of 5 millimeters, then leaving the insulated covering 108 in place produces an ablation volume that typically spares the bladder neck BN. Removing the insulation covering 108 to bring the exposed electrode to within 2 millimeters of the bladder neck results in ablation of the bladder neck by the RF heating.

Figure 4:
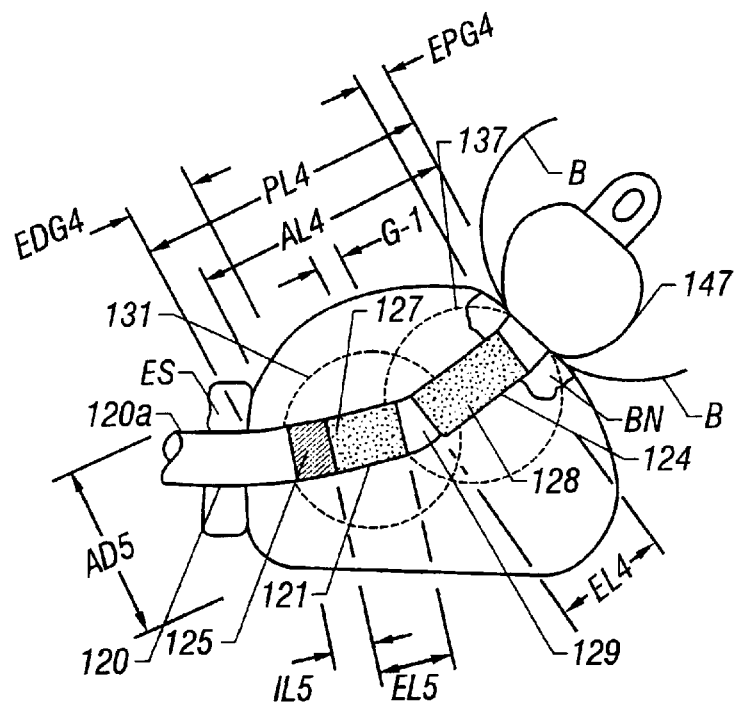
FIG. 4 shows an embodiment of a prostate ablation electrode with multiple electrode elements on a catheter and a selectable, insulative band in accordance with the present invention.

Referring to FIG. 4, a probe 120 includes a urethral catheter 120a made of an insulative rubber material and two electrode segments, 121 and 124, for example, cylindrical metal rings disposed on the external surface of the catheter 120a. The ring 121 has an electrically exposed area 127 and an insulated portion 125. Electrode ring 126 has a completely electrically exposed surface 128. There is a gap G1 of, for example, 3 to 5 millimeters, between the two rings 121 and 124. The length of the exposed area 127 on ring 121 is EL5. The width of the insulative portion 125 is IL5. The length of the exposed conductive area of ring 124 is EL4.

Rings 121 and 124 are coupled to the generator such that the RF generator output can be selectively applied to ring 121 alone, to ring 124 alone, or simultaneously to both rings. If power is applied to ring 121 along, an ablation volume, illustrated by dashed line 131, is produced having a diameter AD5. If electrode 124 is activated separately by the generator RF output, an ablation volume, illustrated by dashed line 137, is produced with a diameter similar to that for the first ring 121. Thus, the independent use of RF heating on ring 121 and then ring 124, sequentially, produces a total ablation volume equal to the sum of the dotted lines 131 and 137, having an ablation length AL4, which is larger than the ablation lengths of each of the independent ablation zones 131 and 137. Thus, elongation of the ablation length is achieved, and the ablation zone has an ablation diameter approximately equal to AD5, which is controllable based on RF parameters for heat ablation on a single ring alone. Furthermore, the gap G1 between the electrodes 121 and 124 can be selected such that the ablation margins 131 and 137 overlap in the gap region 129. Thus there are no missing segments in the ablation volume over the ablation length AL4.

Gap 129 provides a degree of flexibility to probe 120 in the region where the electrodes are mounted to catheter 120a. The urethra as it passes from the external penis to the prostate and then within the prostatic urethra to the bladder takes very significant and relatively sharp turns. If it is desired to have an ablation length AL4 that corresponds to, for example, a 40 millimeter long electrode, the spaced electrodes advantageously provide increased flexibility of the catheter in the region of the electrodes as compared to a single 40 millimeter long electrode to accommodate the natural physiologic curves of the urethra. It is desirable that the gap between the electrodes be long enough to provide flexibility and yet short enough to prevent gaps in the aggregate ablation volume.

Figure 5:
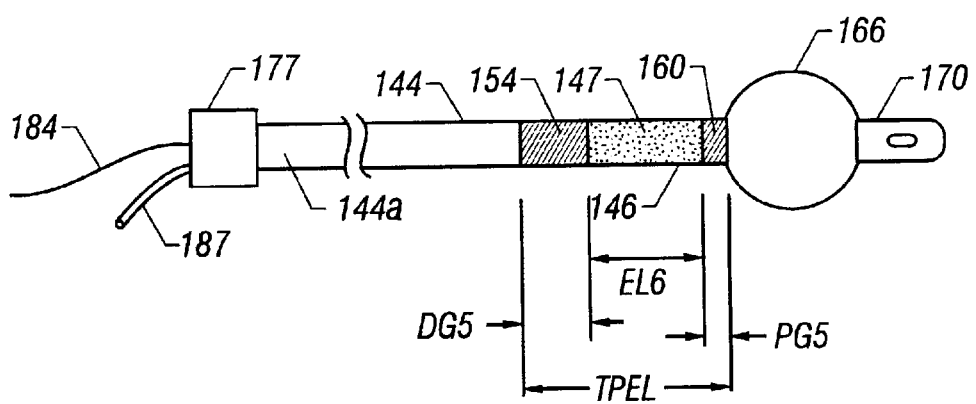
FIG. 5 shows an embodiment of a prostate ablation electrode according to the present invention having a universally adjustable, conductive surface exposure.

Referring to FIG. 5, a probe 144 includes, for example, a catheter 144a and an electrode 146 having a region of exposed electrically conductive surface 147, a proximal insulated segment 160, and a distal insulated portion 154. The total possible electrode length TPEL equals the sum of the exposed area 147 length EL6 plus the length PG5 of the insulated portion 160 and the length DG5 of the distal insulated portion 154. The proximal gap length PG5 can be selected, adjusted, or changed by the surgeon by removing segments of insulation over the portion 160. Similarly, the distal gap DG5 of the insulated area 154 can be varied, selected, or adjusted by the surgeon by removing portions of its insulated covering. The length of conductive surface 147 can also be varied by removing insulation from portions 154 and 160 to match the electrode length to the patient's prostate length.

Electrode 146 can be of various designs, for example, a cylindrical ring on the surface of the probe shaft 144, and the insulation portions 154 and 160 can be insulative tape, heat shrunk on bands, peel-off insulation coatings, or other insulation types. Alternatively, electrode 146 can be a form of conductive wire braid or spiral-wound wire band that has a degree of flexibility, or an end-to-end sequence of annular electrode wires or rings or a mesh or corrugated fenestrated metal cylinder to achieve flexibility. Although the embodiment in FIG. 5 shows a balloon structure 166 with typical catheter drainage end 170, the use of a non-balloon structure and non-flexible structure is within the scope of the invention.

Figure 6:
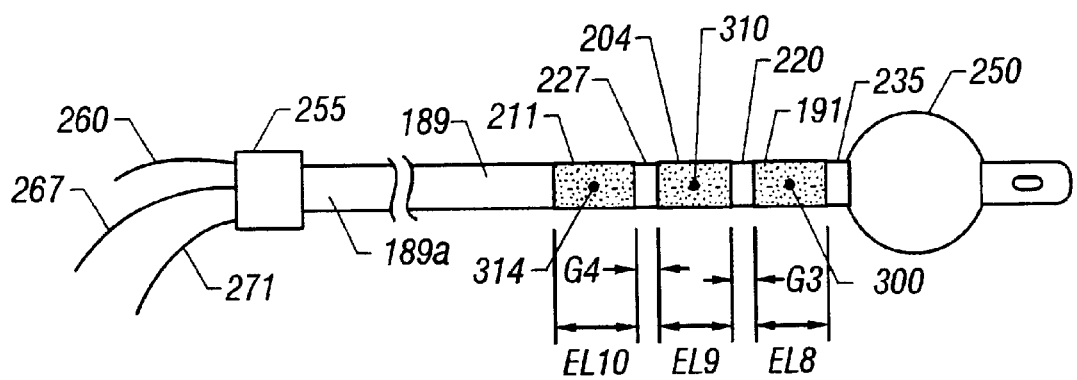
FIG. 6 shows an embodiment of a prostate ablation probe according to the present invention having a multiplicity of conductive elements disposed on the surface of the probe for selectable ablation positioning and length.

Referring to FIG. 6, a probe 189 includes a catheter 189a and three spaced RF electrodes 191, 204, and 211 having exposed surfaces 300, 310, and 314, respectively. Each of the RF electrodes 191, 204, and 211 are separately electrically connected to connections 260, 267, and 271, respectively, near the hub 255 of the catheter. Gap segment 220 between electrodes 191 and 204 and gap segment 227 between electrodes 204 and 211 are electrically non-conductive. These gaps can be part of the underlying flexible rubber structure of catheter 189a. The electrodes can include selectable and/or removable insulative bands or coatings. By selecting to apply power to one, two, or three rings, incremental enlargement of the ablation volume length can be achieved. Thus, the length of the ablation volume can be varied while keeping the ablation diameter approximately constant.

Probe 144 can universally fit a wide range of physiologic prostate lengths. For example, if only ring 191 of 15 millimeter length is activated by RF signal, then an ablation region of about 20 millimeters long is achieved that can accommodate prostate urethras of 20 to 25 or 30 millimeters length. Activating two rings, 191 and 204, in sequences induces an ablation region of 35 to 40 millimeters length that can accommodate prostate urethras of length 35 to 45 millimeters. Activating three rings, 191, 204, and 211, sequentially induces an ablation region of 50 to 55 millimeters in length that can accommodate prostatic urethras of length 50 to 60 millimeters long. Adding insulative coverings on these ring electrodes allows even finer verniations of ablation lengths, and thus finer matching to prostate lengths.

Variations in design of the embodiment in FIG. 6 can achieve universal fitting to various prostate lengths. If prostate lengths of, for example, 25 to 60 millimeters are to be accommodated, and the rings are 10 millimeters long, then four of five rings can be used, with gaps of 2 to 3 millimeters between them. The rings can be activated singly in sequence, or in coupled pairs, or in triplets, or possible all together, depending on the time of the RF application and degree of verniation selected. A probe with 5 to 7 millimeter electrode lengths, and 1, 2, 3, 4, or 5 millimeter gaps may require up to about seven to ten electrode segments to cover the prostate lengths. If 20 millimeter long electrodes are used, then about three electrodes can accommodate a large range of prostate sizes. The longer the individual electrodes, then the less verniation in ablation length is possible, without selectable, adjustable insulation coverings. Mixed lengths of electrode segments can be devised on the probe. Also, various probes can have different numbers of electrode segments to match to various prostate lengths. Electrode segments of 5, 10, 20 or greater millimeter lengths are effective.

Incremental enlargement of the ablation volume can be done without moving the position of the electrode 189 within the urethra or prostate between heating episodes. Using the balloon 250 on the catheter 189a to restrain the catheter against the bladder neck margin assures that the electrode positions remain stably placed in the prostate for the duration of the RF heating. This has a significant advantage in terms of certainty of electrode placement once it has been confirmed by imaging and in terms of safety that undesired movement of the electrodes and therefore undesired ablation locations can be avoided.

Furthermore, if the RF ablations are done individually on each electrode, a degree of incremental control is achieved. The surgeon can produce one heat ablation around one electrode and determine if the patient is in discomfort or if there are any other symptoms providing better control and reduction of risk of injury to surrounding structures. Sequentially applying power to a series of RF electrodes along the length of the urethral catheter lengthens the ablation volume in a controlled way.

Figure 7:
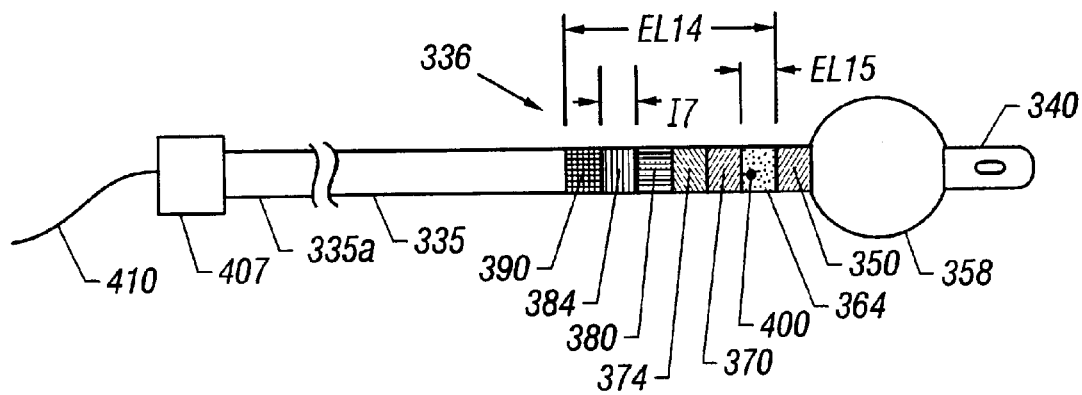
FIG. 7 shows an embodiment of the prostate ablation probe according to the present invention with a multiplicity of selectable insulation bands on the conductive electrode element.

Referring to FIG. 7, a probe 335 includes a catheter 335a and an electrode 336 spanning the length EL14 and including a series of segmented domains. One domain is an exposed, electrically conductive surface 364 having an exposed electrode length EL15. Surface 364 is spaced from the balloon 358 by an insulative gap 350. The gap may have beneath it a conductive structure, and comprise an insulative coating that can be removed in a discrete or continuous way. Toward the direction of the hub 407 there is a series of insulative bands 370, 374, 380, 384, and 390, each having a length 17. Beneath each insulative band is a conductive element which can be connected electrically to the exposed conductive surface 364 or be independently connected via connection wires through the hub 407 as part of connection element 410. A choice of discrete RF electrode lengths is possible, ranging over the length EL14. The insulative bands, such as 370, can be stripped off by a knife or peeled off as with a piece of tape to expose an enlarged RF electrode conductive surface, and thus extending the surface 364. In this way, the length of the RF electrode, as well as the length of the ablation volume, can be tailored to the length of a particular patient's prostate length. The electrode length can be changed while maintaining the use of temperature sensors and without requiring changing of the wiring to the electrode.

Figure 8:
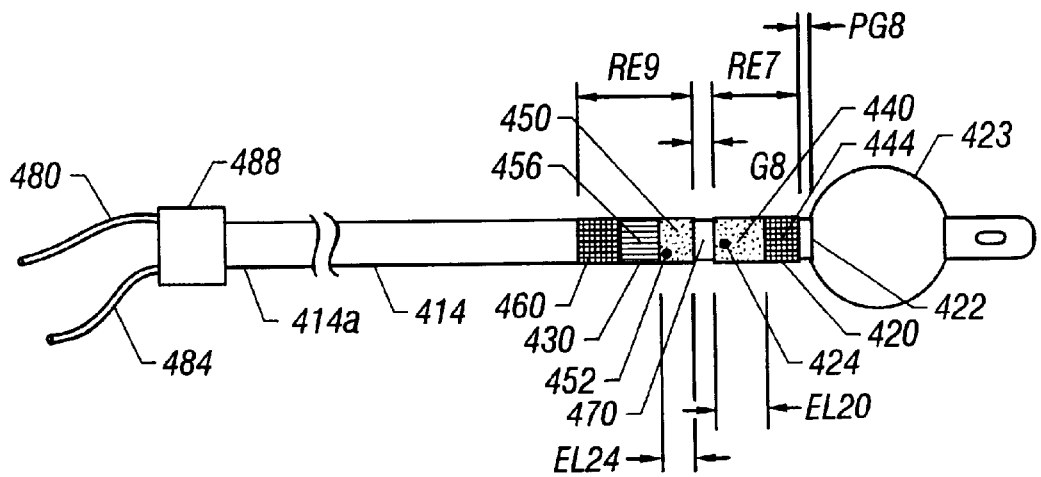
FIG. 8 shows an embodiment of the prostate ablation probe according to the present invention comprising two circumferential electrode rings on a flexible catheter with removable insulative bands and temperature sensors for grading the size and length of ablation volume.

Referring to FIG. 8, a probe 414 includes a urethral catheter 414a and two electrodes 420 and 430 separated by a gap G8. Electrode 420 has an overall length RE7, and is separated by an insulative gap of length PG8 from the proximal margin 422 of the inflatable balloon 423. Electrode 420 has an electrically exposed portion 440 with a length EL20, and a portion 444 covered by insulation. Electrode 430 has an exposed conductive portion 450 with a length EL24, a segment 456 with an insulative coating, and another portion 460 with an insulative coating. The insulative portions 440, 450, and 456 may be of different or varied color or identification so that it is easy to determine which insulation should remain and which should be removed to achieve a desired overall ablation length. For example, the insulative bands may be bands of heat shrink Teflon, which are shrunk on and sized to a prescribed incremental length.

Each of the electrodes 420 and 430 has length of, for example, 15 millimeters. The gap between the electrodes is, for example, approximately 4 millimeters, to provide flexibility and sufficient overlap of independent ablation volumes. The insulative bands 444, 456, and 460 have lengths of, for example, 5 millimeters. Each of the insulative bands can easily be removed by a scalpel or scissors. Furthermore, each electrode 420 and 430 has separate electrical connections 480 and 484, respectively, at the hub 488 of the probe. In use, if the urologist determines that the bladder neck should be ablated, the 5 millimeter long insulative band 444 is removed from the probe prior to insertion. Furthermore, depending on the length of the patient's prostate, the urologist may decide to perform a second RF heating treatment through the electrode 430. The urologist can remove all or portions of one ore more insulation bands, depending on the desired size of the exposed RF electrode 430.

Figure 9:
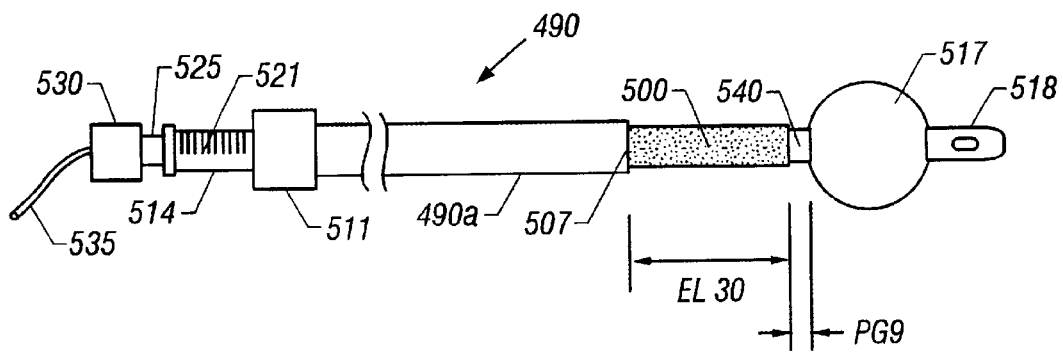
FIG. 9 shows an embodiment of a probe for prostate ablation according to the present invention with a continuously adjustable, exposed electrode length and position.

Referring to FIG. 9, a probe 490 includes an insulative sheath or tube 490a through which an electrically conductive element 500 emerges. Element 500 is, for example, a metal tube or flexible metal structure that slides within sheath 490. Inside RF electrode element 500 is another tubing 540 with a balloon 517 and a distal tip 518 for insertion into the urethra and anchoring to the bladder. The outer sheath 490 has a hub 511, and element 500 has a second hub 514, which slides within hub 511. Hub 514 has scale markings 521 to gauge the degree of extension length EL30 of electrode 500 outside of the distal end 507 of sheath 490. Thus, moving the hub 514 relative to hub 511 changes the length EL30 of exposed electrode 500, and thus the length of the RF ablation can be adjusted according to the prostate length. Tubing 540 has a hub 530, which slides within hub 514. By moving hub 530 relative to hub 514, the length PG9 of the gap between element 500 and balloon 517 can be adjusted according to whether the bladder neck is to be spared or ablated. The electrode structure exposed area 500 is of a flexible construction such as a spiral, braided, multi-ring, segmented, or other flexible metal construction for ease in passage around the curves of the urethra.

The electrode can be positioned appropriately in the prostate by means other than an anchoring balloon. For example, by imaging with ultrasound, CT, MRI, or X-ray, using index markers, impedance measurements of an impedance electrode on the probe distal portion to detect if the electrode is in the bladder, prostate, or outside the prostate, or visual methods such as having the probe comprise an endoscope or fiber optic channel so that direct visualization of the urethra, prostate, bladder, and other landmarks gives direct optical confirmation of proper electrode position.

Figure 10:
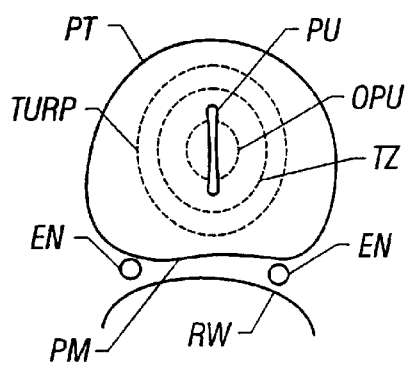
FIG. 10 illustrates a sectional view through the prostate showing a coapted urethral channel.

FIG. 10 illustrates schematically a diagram showing a coronal view through the human prostate and related structures. The prostate PT is shown in a cross-sectional plane that is roughly orthogonal to the prostatic urethra PU. Normally, the prostatic urethra, shown as the solid line PU, is located centrally in the prostate PT and, when the patient is not voiding, is coapted along a vertical line. If the prostatic urethra is opened up to its fullest cross-sectional area, it would approximate a circle, illustrated by the dashed line OPU. The diameter of the open prostatic urethra OPU is nominally 8 millimeters. Nearly all adult prostatic urethras can accept cystoscopes and endoscopes that are 21 to 23 French, i.e., 7 to 8 millimeters, in diameter, and these endoscopes substantially fill the open urethral passage.

The prostate is a complex of glandular and muscle-like tissue. It has a tissue interface called the "transition zone" at about a 10 millimeter diameter around the urethra. This is indicated by the dashed line TZ. In a surgical TURP procedure, the objective is to surgically cut out a margin of tissue around the urethra, yielding a cavity of a minimum 20 millimeters in diameter, indicated by the dashed line TURP in FIG. 10. This TURP diameter is sufficient to inhibit re-obstruction of the prostate due to advancing BPH disease, and to remove all the material in the transition zone TZ. The posterior margin PM of the prostate is only 3 or 4 millimeters from the rectal wall RW. It is important that the TURP margin does not break through the posterior margin because the rectal wall is a highly critical and sensitive structure. The erectile nerves EN run bilaterally between the prostate posterior margin PM and the rectal wall RW. Avoidance of these critical structures during TURP is very important to preserve sexual function.

Figure 11:
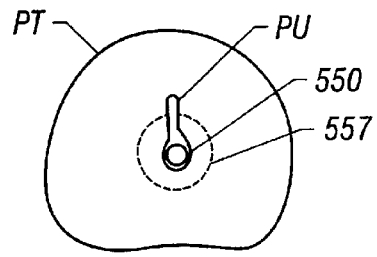
FIG. 11 illustrates a sectional view through the prostate with a small size ablation probe within the prostatic urethra.

FIG. 11 illustrates the use of a radio-frequency electrode 550 having a diameter less than approximately 16 French (5.3 millimeters), which does not completely fill the prostatic urethra PU. Thus, the electrode resides in a portion of the partially coapted urethra PU, and the electrode surface does not make substantially full electrical contact with the urethral tissue. This has the disadvantage that the ablation margin, as illustrated by the dashed line 557, is asymmetrically located with respect to the urethra PU. This runs the risk of inadequate envelopment of the peri-urethral region and re-collapse of the urethral channel under BPH pressure. Furthermore, for a specified temperature of tissue next to the electrode during RF heating, the diameter of the ablation zone 557 is smaller for smaller electrodes. Thus unacceptable or dangerously high core temperatures are required to achieve ablation diameters that approach the effectiveness of that for TURP, resulting in the dangers of unpredictable thermal distributions, focal boiling, charring, gas formation, and unwarranted thermal spread to critical structures increases.

Figure 12:
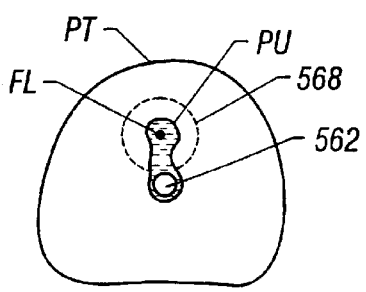
FIG. 12 illustrates a sectional view through the prostate with a small size probe within the prostatic urethra and also fluid within the urethra.

Referring to FIG. 12, another difficulty that can be encountered with a small electrode that does not fully occlude the urethra PU is the welling up or flow of fluid FL into the urethra PU in the unoccluded area of PU. The fluid FL likely includes urine, an electrically conductive electrolyte. Thus during RF heating from electrode 562, there is potentially a shunt pathway of the RF current through the fluid FL and out into peri-urethral tissue that is closest to the fluid producing unknown and unpredictable spread of RF current with unacceptable variability of heating direction and range. Furthermore, urine passing from the bladder down the urethra past the electrode provides an electrolytic pathway of RF current and of heat, downstream and potentially upstream in the urethra. This can have safety consequences, since the heat can spread to critical structures such as the external sphincter or external urethra, leading to serious complications.

Figure 13:
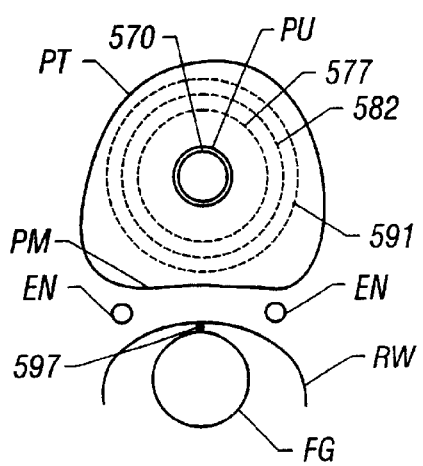
FIG. 13 illustrates a sectional view of the prostate with an occlusive ablative electrode within the urethra and accompanying zones of ablation in accordance with the present invention.

Referring to FIG. 13, according to the invention, an RF electrode 570 has a diameter that substantially occludes the fully distended prostatic urethra PU. Urethra PU lies immediately outside of and in contact with the electrode 570 over substantially all of the electrode's surface such that the electrode is in significant mechanical and electrical contact with the urethra during RF ablation. Thus, with the occlusive RF electrode, more complete electrode contact to the urethral wall is achieved, resulting in more effective and symmetrical heating of peri-urethral tissue, and the chance of fluid pooling or flowing between the electrode 570 and the urethra PU is reduced.

The RF electrode 570 is, for example, a circumferential, electrically conductive ring having a diameter in the range of about 16 French (5.3 millimeters) to 24 French (8 millimeters) or more. There is some variation in urethral size among patients, but nearly all can accommodate, for example, a 20 to 23 French endoscope. Thus, for example, for smaller diameter prostates, a 17 to 20 French (5.6 to 6.6 millimeter) diameter electrode is appropriate. For nominal prostates, a 20 to 22 French (6.6 to 7.3 millimeter) diameter electrode 570 is appropriate. For larger prostates, electrode diameters of 7, 8, or 9 millimeters, or 22, 24, 26, or 28 French are appropriate. Nominally, an electrode diameter of 7 to 8 millimeters would be occlusive to a substantial degree for most human prostatic urethras.

Dashed lines 577, 582, and 591 schematically represent ablation margins from RF heating using electrode 570. Thermal mapping measurements done using ex-vivo human prostates heated with an RF electrode having an outer diameter of 7.4 millimeters and an electrode length of 10 to 15 millimeters, and applying RF power to raise the tissue temperature at the electrode/tissue interface to 70° C. for three minutes produced an ablation diameter of approximately 18 to 20 millimeters. The distribution around the electrode is approximately symmetrical, as shown by dashed line 577. Ex-vivo measurements indicate that if increased RF power is applied to the same electrode to raise peri-urethral tissue to 80° C., an ablation diameter of about 24 to 28 millimeters is achieved, as represented by the dashed line 582. Increasing the RF power to achieve higher peri-urethral temperatures of 90° C. further increases the radius of ablation to larger diameters, as illustrated by line 591.

By using occlusive RF electrodes and modest core peri-urethral temperatures of about 70° C. for short times such as three minutes, ablation diameters comparable to the diameters resected in TURP surgery are achievable less invasively and less traumatically than in TURP. Furthermore, by applying high frequency or radio-frequency power to the electrode, heat energy is deposited directly in the prostatic tissue at a distance from the electrode, causing immediate temperature rise at longer distances from the electrode. Thus large ablation volumes comparable to those of TURP are achieved in very short treatment times, for example, approximately three minutes, which limits the chance of spread of unwanted heat to critical structures such as erectile nerves, the rectum, the external sphincter, and internal sphincter. With shorter times, risk of electrode movement during the heating is limited.

RF exposure times of a few minutes in the range of 1 to 5 minutes are desirable. Prostate anatomy indicates use of various temperature and time parameters for RF heating. For example, for larger prostates, longer times such as 5, 7, 10, 15 or 20 or more either in one episode or sequentially increasing time can be used to adequately achieve desired prostate ablation volume. Also, variations in selected core temperatures can vary depending on prostate size. Core temperatures of about 60° C., 65° C., 70° C., 75° C., 80° C., 85° C., 90° C., 95° C., or 100° C., or any temperatures within that range, can be selected to accommodate prostate volume and size.

A digital rectal thermometry can be used to monitor rectal wall RW temperature during RF heating. As shown in FIG. 13, the clinician uses a finger FG to position a temperature sensor 597 against wall RW at a position near the posterior margin PM of prostate PT. A temperature rise above a warning level such as 40 to 45° C. signals to the urologist that unwanted RF heating is spreading near the rectal wall RW, and that RF power should be reduced or turned off.

Figure 14:
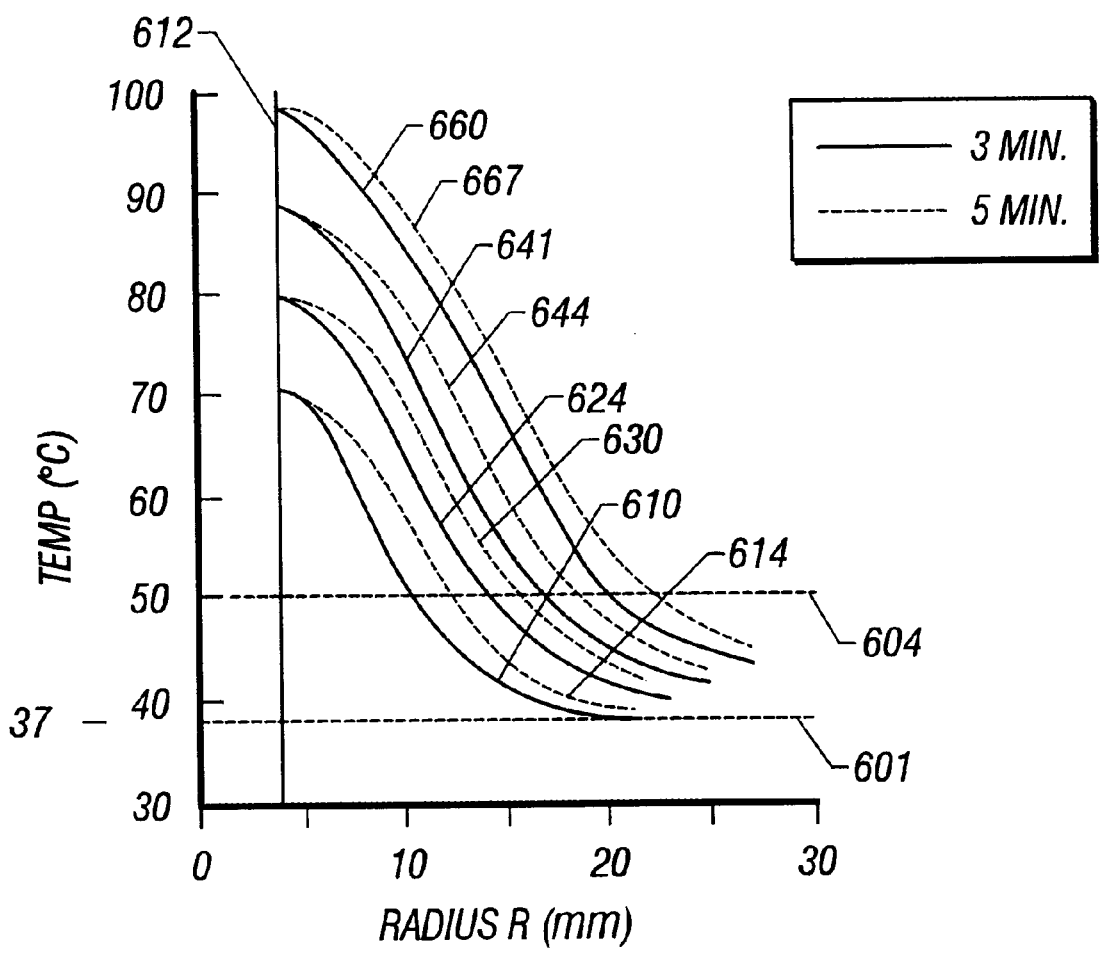
FIG. 14 illustrates the temperature distribution versus the distance from the electrode for a prostate ablation electrode at various power and time parameters in accordance with the present invention.

FIG. 14 illustrates the temperature distribution in the tissue as a function of distance from the electrode. An RF electrode was inserted ex-vivo into human prostatic urethra and RF energy supplied to raise the measured temperature at the surface of the electrode. Line 612 indicates the radius of the electrode. For an RF electrode of approximately 23 French (7.7 millimeters), with a temperature at the surface of the electrode of 70° C., and three minutes of RF heating, the resulting measured data on the distribution of temperature is shown by curve 610. The temperature is plotted as a function of the radius R in millimeters from the center of the electrode. Body temperature is 37° C., shown as the dashed horizontal line 601, which is asymptotically approached by curve 610 for large radius R. The minimum temperature of 50° C. at which ablation occurs is another horizontal line 604. The intercept of line 604 with curve 610 corresponds to a radius R of approximately 10 millimeters or a diameter of 20 millimeters. Repeating the measurement for an RF heating time of 5 minutes, keeping the electrode temperature at 70° C. results in the dashed curve 614. The ablation radius in this case has moved out to approximately 12 millimeter radius or 24 millimeters diameter. Similar measurements with an electrode surface temperature of 80° C. are shown by curve 624, corresponding to an ablation diameter of approximately 28 to 30 millimeters for a three minute RF heating, and 30 millimeters for a heating time of 5 minutes, curve 630. Curves 641 and 660 are extrapolations for electrode surface temperatures of 90° C. and 100° C., respectively, corresponding to three-minute treatment time, and curves 644 and 677, respectively, corresponding to five-minute RF treatments. It is possible to achieve an equivalent ablation radius by different combinations of electrode radius, electrode surface temperature, and the time duration of the RF treatment.

Electrode examples described above are of conductive, exposed metallic rings disposed on the surface of a flexible catheter. Such rings can be extremely thin and non-cooled to achieve an effective clinical result, and can be of a variety of materials, including stainless steel, titanium, cobalt or nickel alloys, or plated copper. Other materials can be used that are embedded in or adhered to the underlying substrate of the catheter including conductive plastics, conductive silicone sheets, braided wire structures that are embedded into the plastic substrate of the catheter, circumferential wires, helices, longitudinal wires, conductive foils or films, meshes of wire, and other variations. The RF electrode structures can have desirable properties for imaging, for example, roughened, etched, pitted, or sand blasted surfaces to enhance echo-genicity for ultrasonic imaging, low-density material for CT or X-ray images to give appropriate contrast relative to anatomy, MRI-suitable material such as titanium, aluminum, cobalt or nickel alloys, copper, or other conductors or metals that enable visualization without artifact in MRI images.

Electrical connections can be made in the monopolar, bipolar, or multi-polar arrangements with the external RF generator to achieve a variety of electric field and current patterns around the RF electrodes, and thus achieve variations in heating patterns around or between the electrodes. For a bipolar arrangement, the heating pattern tends to be more intense in the gap between the electrode and less intense towards the extreme end regions of the electrodes. The gap between the electrodes could thus be widened into the ranges of 5 to 10 millimeters, 10 to 15 millimeters, or 20 or more millimeters.

Referring again to FIG. 8, an elderly patient has been treated with a catheter/electrode system similar to that shown in FIG. 8. The patient had been in retention (could not urinate) for over six months, and was required to have an indwelling drainage catheter in his urethra during that period. Because he had severe heart and lung problems, TURP surgery was not indicated. A 20 French, flexible silicone balloon catheter with two 15 millimeter long stainless steel rings with outer diameters of approximately 7.7 millimeters secured to the exterior surface of the catheter was used in the procedure. The gap PG8 between the ring 420 and balloon 423 was 2 millimeters. The length of insulation band 444 was 5 millimeters. The gap G8 between the rings was 4 millimeters. Initially, the exposed portion EL24 was 5 millimeters, and the two separate insulative bands 456 and 460 were each 5 millimeters long. Thermocouple thermal sensors were roughly in the positions 424 and 452. Based on the length of the patient's prostate and other considerations, the insulation band 444 was kept on ring 420 so as to preserve the bladder neck. Second ring 430 was activated in a sequential manner, and the insulation 456 was removed so that the total exposed electrode for the second ring 430 was 10 millimeters.

RF heating with ring 420 at 70° C. was performed for three minutes. Subsequently, RF heating with ring 430 at 70° C. was performed for 3 minutes. The RF generator monitored the RF power output, the temperature associated with each ring, and the impedance of the electrodes to be sure they were in reasonable parameters before RF power was delivered. No general anesthesia was required. After removal of the catheter, the patient was sent home that day with a standard drainage catheter in place. Two weeks later the drainage catheter was removed, and the patient was able to void (urinate) voluntarily and freely for the first time in over six months. Signs of necrotic prostatic tissue was observed in his urine, indicating that the tissue in the ablated volume that had been killed by the RF heating had disintegrated and was being flushed out as debris in the patient's urine stream.

Figure 15:
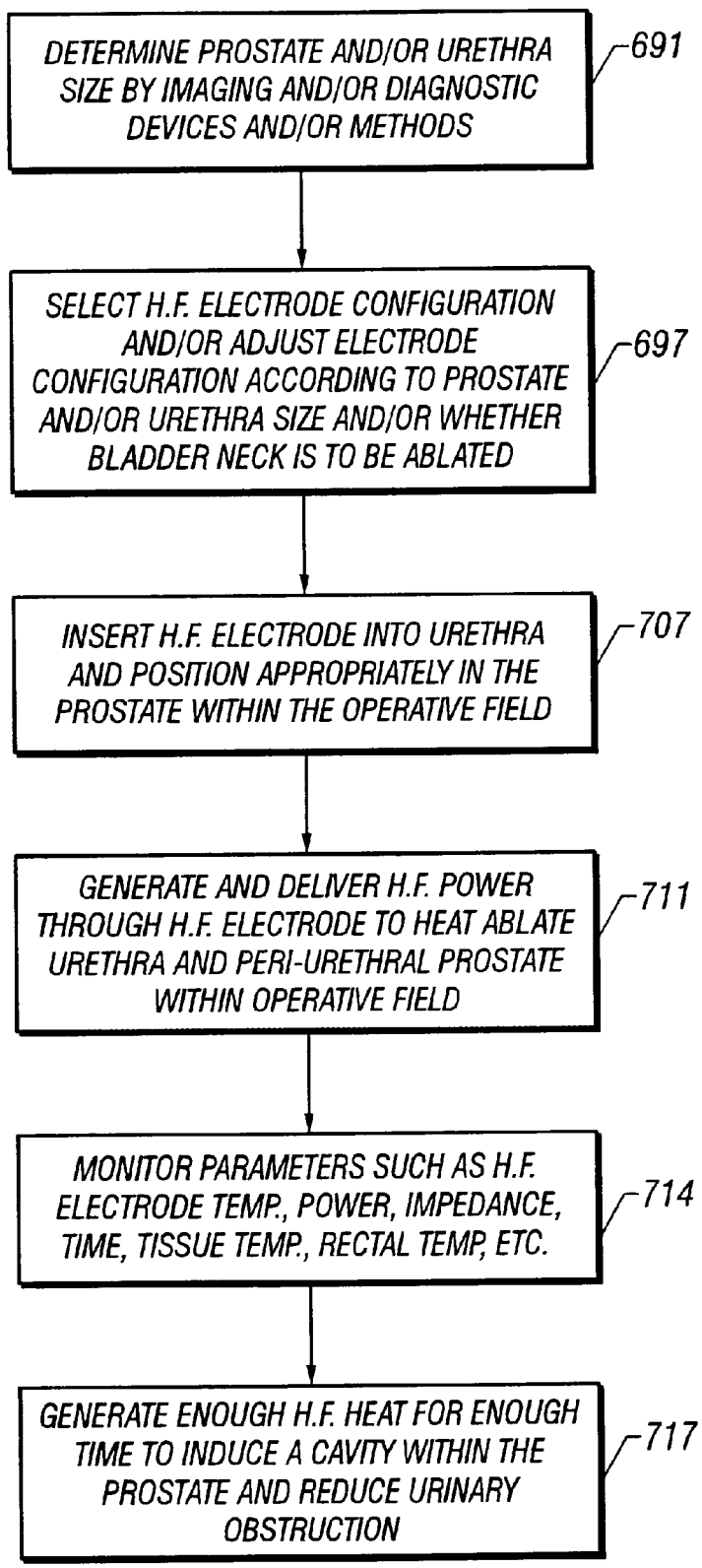
FIG. 15 shows a flow chart of the process employing, in operation, a system in accordance with the present invention.

Referring to FIG. 15, the procedure starts by determining the relevant dimensions of the prostate, and/or the prostatic urethra, and/or any irregularities of the urethra such as strictures, obstructions, and/or the diameter of the urethra, and/or the geometry of the urethral path, including irregularities (step 691). For example, the length of the prostatic urethra from the verumontanum to the bladder neck can be determined by various imaging and diagnostic methods, including an endoscope or urethroscope inserted into the urethra to directly observe the length, CT or MR imaging, X-ray imaging contrast, or trans-urethral ultrasound. The anterior-to-posterior size of the prostate in circumference or volume can be made in step 691. Step 691 can also include clinical decisions as to whether the bladder neck should be preserved according to patient wishes, age, or other considerations. The desired ablation length is then determined.

The next step is selection of the high frequency electrode configuration and/or adjustment to the electrode configuration based on prostate dimensions and the desired RF ablation volume (step 697). For example, in this step, one or several RF electrodes are selected, and the length and diameter of the individual electrodes are selected, with removal of insulative bands if required. The configuration of the catheter is also selected, for example, a flexible urethral catheter having an irrigation aspiration port and a balloon, or a non-balloon catheter, an endoscopic structure with optical viewing, irrigation, aspiration, and manipulation functions and one or more RF electrodes disposed on the surface of the endoscopic probe or projecting forward of the endoscopic probe, as through an inner lumen of the probe.

The next step is inserting the high frequency probe into the urethra (step 707). Urine is flushed from the bladder, and plain water without ionic content is infused into the bladder prior to RF heating. If the catheter has a balloon on its distal end, the balloon is then inflated and the catheter pulled so that the balloon is snugly placed at the bladder neck. Diagnostic imaging can be used to confirm that the catheter, balloon, and/or electrodes are in the proper position, and observation made of index markings on the catheter at the external urethra entrance.

In step 711, the application of high frequency power is initiated. In step 714, for example, the RF electrode temperature, RF power, current, voltage, impedance, and time of power application are monitored before, during, and/or after the RF heating process. Monitoring of impedance of the RF electrode gives an instant check of circuit continuity or any untoward situation that may occur relative to the electrode. In step 717, the RF ablation parameters and time duration of the RF heating are applied to induce a cavity within the prostate that achieves the desired clinical result.

Other embodiments are within the scope of the following claims.

What is claimed is:

1. A device for enlarging a urethral passage, comprising:
an elongate member having a distal portion configured for intraurethral placement in the urethral passage, and
an electrode at the distal portion of the elongate member configured to be energized with high frequency energy to necrose tissue of the urethral wall and surrounding prostate tissue to form a cavity in the urethral passage, the electrode having an adjustable working length.

2. The device of claim 1 further comprising a removable insulative member covering at least a portion of the electrode.

3. The device of claim 1 further comprising an insulating sleeve, the electrode being movable relative to the insulating sleeve to adjust the working length.

4. The device of claim 1 wherein the electrode has a diameter greater than about 16 French to substantially occlude the urethra.

5. The device of claim 1 wherein the electrode is disposed on an outer surface of the distal portion of the elongate member.

6. The device of claim 1 comprising multiple electrodes at the distal portion of the elongate member, at least one of the electrodes having the adjustable working length.

7. The device of claim 6 further comprising multiple wires, each wire for independently coupling one of the multiple electrodes to a high frequency electrical signal.

8. The device of claim 6 wherein the electrodes are spaced apart a distance of about 1 to 5 mm.

9. A device for enlarging a urethral passage, comprising
an elongate member having a distal portion configured for intraurethral placement in the urethral passage, and
a plurality of electrodes at the distal portion of the elongate member configured to be energized with high frequency energy to necrose tissue of the urethral wall and surrounding prostate tissue to form a cavity in the urethral passage, the electrodes being spaced apart a distance of about 1 to 5 mm to provide flexibility in the distal portion of the elongate member.

10. The device of claim 9 wherein the electrodes have a diameter greater than about 16 French to substantially occlude the urethra.

11. The device of claim 9 further comprising multiple wires, each wire for independently coupling one of the multiple electrodes to a high frequency electrical signal, whereby said high frequency electrical signal can be selectively applied to each of the electrodes to adjust a length of the region of ablative heating.

12. The device of claim 9 wherein the electrodes are disposed on an outer surface of the distal portion of the elongate member.

13. The device of claim 9 further comprising a removable insulative member covering at least a portion of one of the electrodes.

14. A method of treating a urethral passage, comprising:
measuring a length of a patient's prostate, and
selecting a length of an electrode based on the measured length of the prostate, the electrode being configured to be energized with high frequency energy to necrose tissue of the urethral wall and surrounding prostate tissue to form a cavity in the urethral passage.

15. The method of claim 14 wherein the electrode comprises multiple electrodes and the step of selecting includes determining which electrode to energize.

16. The method of claim 14 wherein the step of selecting includes removing insulation from the electrode.

17. The method of claim 14 wherein the step of selecting includes advancing an electrode relative to an insulating sleeve.

18. The method of claim 14 further comprising selecting a diameter of the electrode that substantially occludes the urethra.

19. The method of claim 14 further comprising energizing the electrode with high frequency energy to elevate the temperature of the urethra to at least 50° C. to ablate tissue of a wall defining the urethral passage and ablate adjacent prostate tissue to form a cavity communicating with the urethral passage.

20. The method of claim 14 wherein selecting a length of the electrode includes adjusting a working length of the electrode.

* * * * *